United States Patent [19]

Edwards et al.

[11] Patent Number: 5,393,743
[45] Date of Patent: Feb. 28, 1995

[54] ERYTHROMYCIN DERIVATIVES

[75] Inventors: Carla Edwards, Evanston; Paul A. Lartey, Wadsworth, both of Ill.

[73] Assignee: Abbott Laboratories, Abbott Park, Ill.

[21] Appl. No.: 87,547

[22] Filed: Jul. 6, 1993

[51] Int. Cl.$^6$ .................. A61K 31/70; C07H 17/04
[52] U.S. Cl. ........................... 514/29; 536/7.2
[58] Field of Search ........................... 536/7.2; 514/29

[56] References Cited

U.S. PATENT DOCUMENTS 4,514,562   4/1985   Toscano ...................... 536/7.2

Primary Examiner—John W. Rollins
Assistant Examiner—Elli Peselev
Attorney, Agent, or Firm—Andreas M. Danckers

[57] ABSTRACT

Antibacterial compounds having the formula

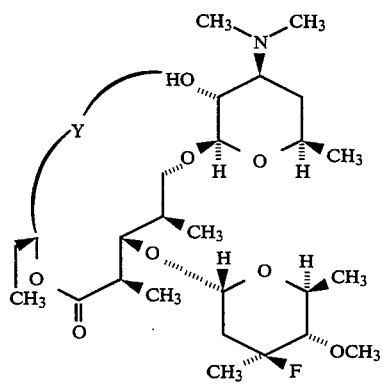

and pharmaceutically acceptable salts thereof, wherein Y is selected from

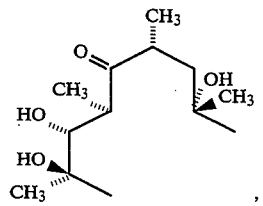

,

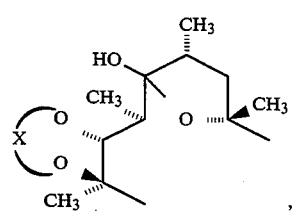

, and

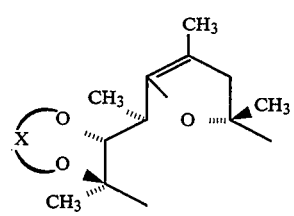

and X is selected from the group consisting of —C(O)—, —C(S)—, —CH$_2$—, —CH$_2$CH$_2$— and —C(CH$_3$)$_2$—; also disclosed are processes and intermediates useful in the preparation of the above compounds, as well as compositions containing the same and methods for their use.

6 Claims, No Drawings

ERYTHROMYCIN DERIVATIVES

TECHNICAL FIELD

The present invention relates to novel semisynthetic macrolides having antibacterial activity and useful in the treatment and prevention of bacterial infections. More particularly, the invention relates to C-3″-fluoro derivatives of erythromycin A, processes for their preparation, compositions containing such compounds and methods for using the same.

BACKGROUND OF THE INVENTION

Erythromycins A through D, represented by formula (I) below,

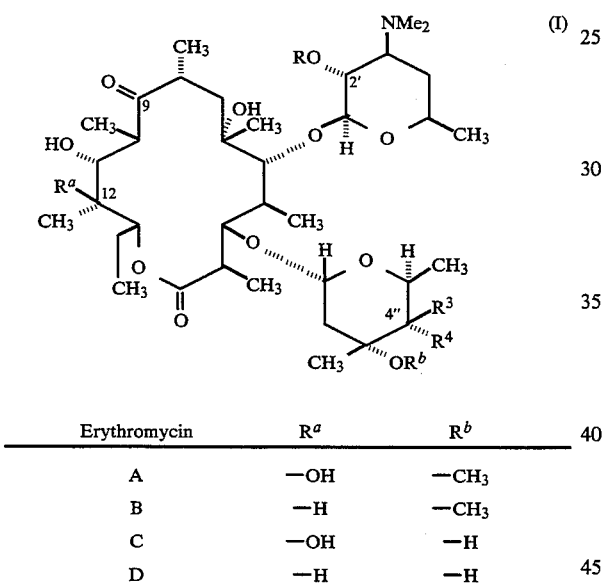

| Erythromycin | $R^a$ | $R^b$ |
|---|---|---|
| A | —OH | —CH$_3$ |
| B | —H | —CH$_3$ |
| C | —OH | —H |
| D | —H | —H | are well-known and potent antibacterial agents. Erythromycin A in particular is widely used to treat and prevent bacterial infection. As with other antibacterials, however, bacterial strains having resistance or insufficient susceptibility to erythromycin have been identified. Another drawback of erythromycins is their poor acid stability, which sometimes results in poor or unpredictable oral absorption. Consequently, numerous investigators have sought to prepare chemical derivatives of erythromycin in an attempt to obtain analogs having modified or improved profiles of antibiotic activity.

SUMMARY OF THE INVENTION

The present invention comprises novel derivatives of erythromycin having the formula

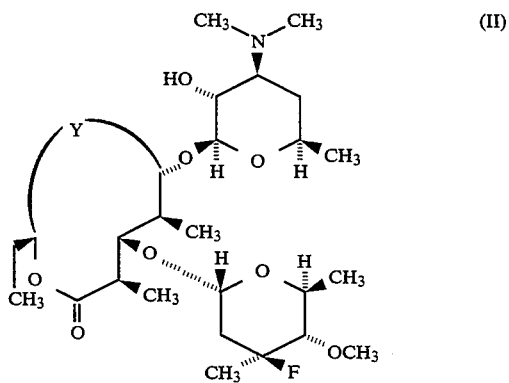

and pharmaceutically acceptable salts thereof, wherein Y is selected from the group consisting of

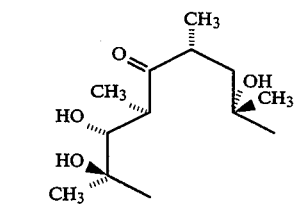

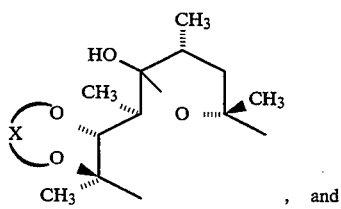
, and

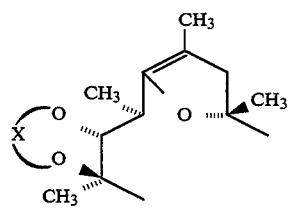

and X is selected from the group consisting of —C(O)—, —C(S)—, —CH$_2$—, —CH$_2$CH$_2$— and —C(CH$_3$)$_2$—.

The present invention also comprises synthetic processes for the preparation of the compounds of the invention, as well as novel intermediates useful therein which have the formulae

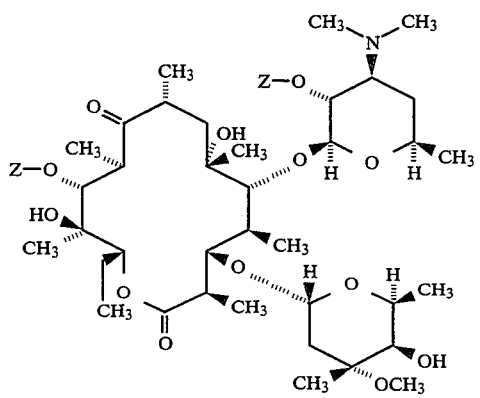

(III)

or

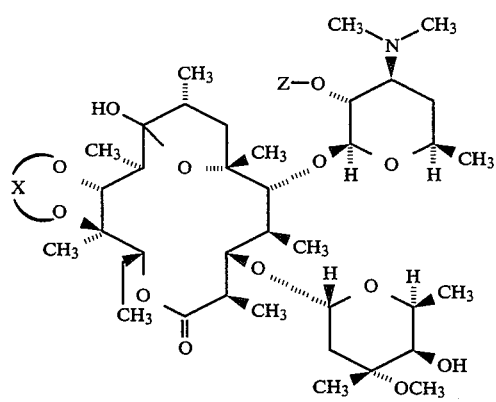

(IV)

wherein X is selected from the group consisting of —C(O)—, —C(S)—, —CH$_2$—, —CH$_2$CH$_2$— and —C(CH$_3$)$_2$— and Z is hydrogen or a suitable protecting group, such as acetyl.

The intermediates of formulae (III) and (IV) are prepared by the selective protection of various reactive sites of erythromycin A, followed by oxidation at the 4″-position to an oxo functionality and then catalytic hydrogenation at the 4″-position. These intermediates are readily converted, by derivatization at positions 3″ and 4″ and deprotection, into the compounds of formula (II).

Because of their antibacterial activity, it is anticipated that the compounds of the present invention will be useful as pharmaceutical agents or industrial disinfectants. It is further anticipated that the compounds of the present invention will have enhanced acid stability. Accordingly, the invention also comprises compositions useful in the treatment and prevention of bacterial infection, comprising a therapeutically effective amount of a compound of formula (II) in combination with a pharmaceutically acceptable carder.

The invention further comprises a method for treating and preventing bacterial infections in humans and other mammals, comprising administering to a patient in need of such treatment a therapeutically effective amount of a compound of the invention for such time as is necessary to achieve the desired therapeutic effect.

DETAILED DESCRIPTION OF THE INVENTION

In one aspect of the present invention are disclosed compounds of the formula

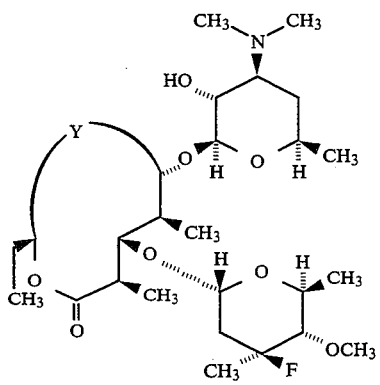

(II)

and pharmaceutically acceptable salts thereof, wherein Y is selected from the group consisting of

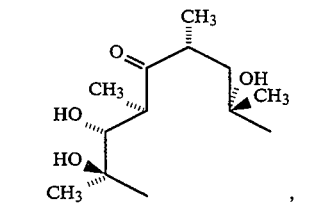

,

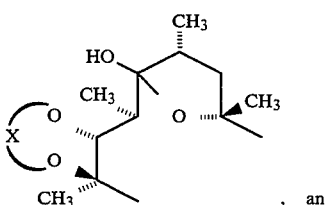

, and

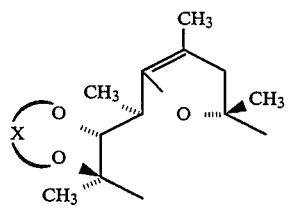

and X is selected from the group consisting of —C(O)—, —C(S)—, —CH$_2$—, —CH$_2$CH$_2$— and —C(CH$_3$)$_2$—.

In another aspect of the present invention are disclosed compounds of the formulae

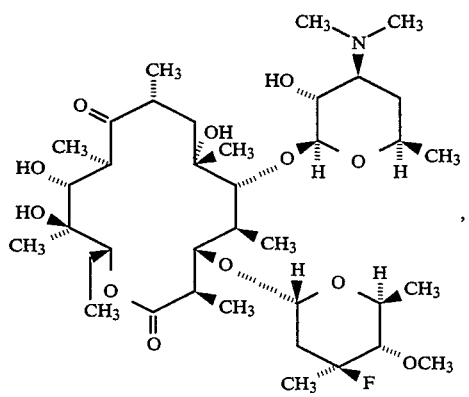

,

-continued

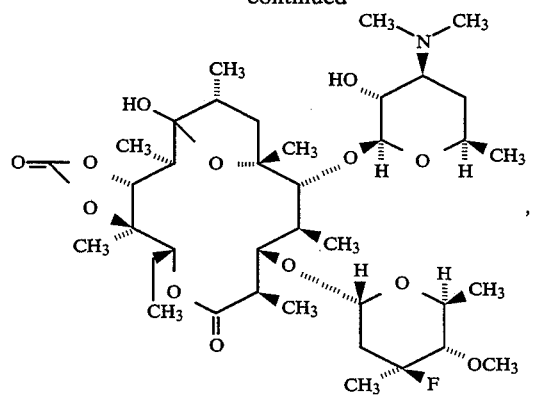

and

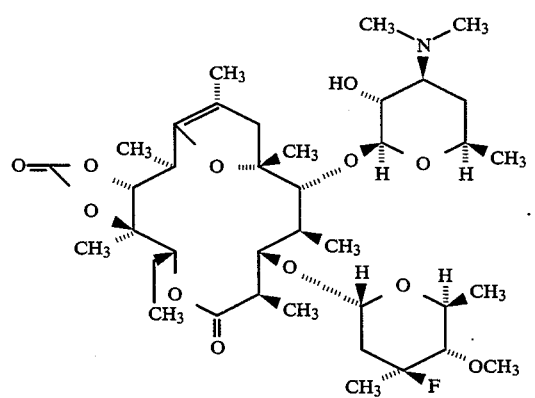

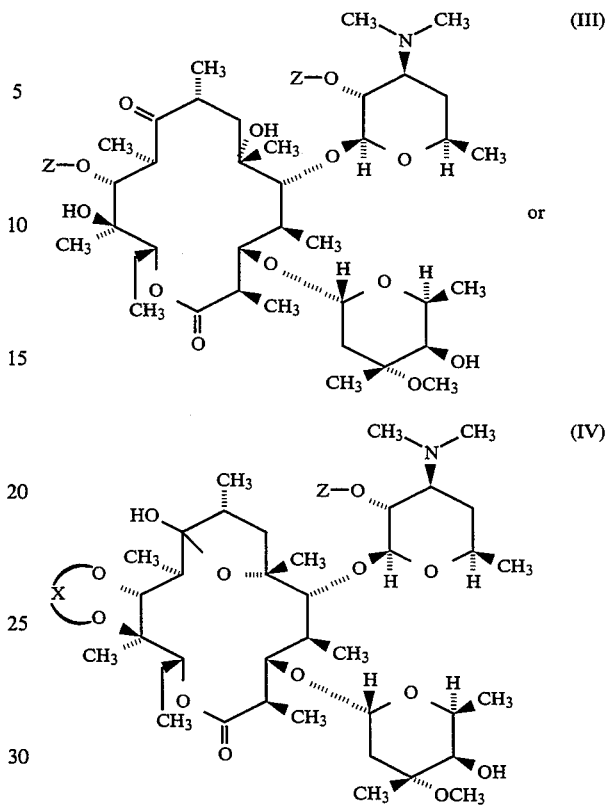

wherein X is selected from the group consisting of —C(O)—, —C(S)—, —CH₂—, —CH₂CH₂— and —C(CH₃)₂— and Z is hydrogen or a suitable protecting group, such as acetyl.

Representative examples of the compounds of the present invention include the following:
(3″S)-3′-Desmethoxy-3″-fluoro-4″-O-methylerythromycin A;
(3″S)-11-O,12-O-Carbonyl-3″-fluoro-3″-desmethoxy-4″-O-methylerythromycin A;
(3″S)-8,9-Anhydro-11-O,12-O-carbonyl-3″-fluoro-3″-desmethoxy-4″-O-methylerythromycin A-6,9-hemiketal;
(3″S)-11-O,12-O-Thiocarbonyl-3″-fluoro-3″-desmethoxy-4″-O-methylerythromycin A;
(3″S)-8,9-Anhydro-11-O,12-O-thiocarbonyl-3″-fluoro-3″-desmethoxy-4″-O-methylerythromycin A-6,9-hemiketal;
(3″S)-11-O,12-O-Isopropylidene-3″-fluoro-3″-desmethoxy-4″-O-methylerythromycin A;
(3″S)-8,9-Anhydro-11-O,12-O-isopropylidene-3″-fluoro-3″-desmethoxy-4″-O-methylerythromycin A-6,9-hemiketal;
(3″S)-11-O,12-O-Ethylene-3″-fluoro-3″-desmethoxy-4″-O-methylerythromycin A;
(3″S)-8,9-Anhydro-11-O,12-O-ethylene-3″-fluoro-3″-desmethoxy-4″-O-methylerythromycin A-6,9-hemiketal;
(3″S)-11-O,12-O-Methylene-3″-fluoro-3″-desmethoxy-4″-O-methylerythromycin A; and
(3″S)-8,9-Anhydro-11-O,12-O-methylene-3″-fluoro-3″-desmethoxy-4″-O-methylerythromycin A-6,9-hemiketal.

In yet another aspect of the present invention are intermediates useful in the preparation of the above compounds and having the formulae Representative examples of the intermediates of the invention include the following:
2′-O-Acetyl-erythromycin A;
2′-O-Acetyl-4″-O-benzyloxycarbonyl-erythromycin A;
2′,11-Di-O-acetyl-4″-O-benzyloxycarbonylerythromycin A;
2′,11-Di-O-acetylerythromycin A;
2′,11-Di-O-acetyl-4″-deoxy-4″-oxoerythromycin A;
2′,11-Di-O-acetyl-4″-epierythromycin A;
(3″S)-2′,11-Di-O-acetyl-3″-desmethoxy-3″-fluoro-4″-O-methylerythromycin A;
(3″S)-11-O-Acetyl-3″-desmethoxy-3″-fluoro-4″-O-methylerythromycin A;
11-O,12-O-carbonylerythromycin A;
2′-O-Acetyl-11-O,12-O-carbonylerythromycin A;
2′-O-Acetyl-11-O,12-O-carbonyl-4″-deoxy-4″-oxo-erythromycin A;
2′-O-Acetyl-11-O,12-O-carbonyl-4″-epierythromycin A;
(3″S)-2′-O-Acetyl-11-O,12-O-carbonyl-3″-fluoro-3″-desmethoxy-4″-O-methylerythrom A; and
(3″S)-2′-O-Acetyl-8,9-anhydro-11-O,12-O-carbonyl-3″-fluoro-3″-desmethoxy-4″-O-methylerythromycin A-6,9-hemiketal.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences,* 66: 1–19 (1977). The salts can be prepared in situ during the final isolation and purification of the compounds of the invention, or separately by macring the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, $p$-toluenesulfonate, undecanoate, valeram salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyates, acrylates, and ethylsuccinates.

Asymmetric centers may exist in the compounds of the present invention. The present invention contemplates the various stereoisomers and mixtures thereof. Starting compounds of particular stereochemistry are either commercially available or are made by the methods detailed below and resolved by techniques well known in the organic chemical arts.

In another aspect of the present invention are disclosed pharmaceutical compositions comprising a therapeutically effective amount of a compound of the present invention formulated together with one or more non-toxic pharmaceutically acceptable carders. As used herein, the term "pharmaceutically acceptable carrier" means a non-toxic, inert solid, semi-solid or liquid filler, diluent, encapsulating material or formulation auxially of any type. Some examples of materials which can serve as pharmaceutically acceptable carders are sugars such as lactose, glucose and sucrose; starches such as corn starch and potato starch; cellulose and its derivatives such as sodium carboxymethyl cellulose, ethyl cellulose and cellulose acetate; powdered iragacanth; malt; gelatin; talc; excipients such as cocoa butter and suppository waxes; oils such as peanut oil, cotton seed oil; safflower oil; sesame oil; olive oil; com oil and soybean oil; glycols; such a propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgement of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly Used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cotton seed, ground nut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-initating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and:shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In a further aspect of the present invention is disclosed a method for treating or preventing bacterial infections in a human or lower mammal, comprising administering to a patient in need of such treatment or prophylaxis a therapeutically effective amount of a compound of the invention, for such time as is necessary to achieve a therapeutic effect. By a "therapeutically effective amount" of the compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.001 to 50 mg/kg body weight or more usually from 0.01 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in multiple doses or in a single dose of from 10 mg to 1000 mg.

In yet another aspect of the present invention are disclosed processes useful in the preparation of the above compounds. In general, the 4"-hydroxyl group of erythromycin or its derivative is selectively oxidized. For example, the 11-hydroxyl group of an erythromycin derivative, having a 2'-O- protecting group, is further selectively protected. Alternatively, an erythromycin derivative having an 11,12-O-cyclic protecting group is further protected at the 2'-O-position. This enables selective oxidation of the 4"-hydroxyl group to afford a 4"-ketone. Reduction of the ketone is performed under conditions that lead to a 4"-epi-hydroxyl intermediate, setting up the stereochemical relationship between the 4"-hydroxyl group on the one hand and the 3"-methoxyl group on the other, necessary for the synthesis of compounds of this invention. It is the treatment of such a 4"-epihydroxyl intermediate with fluorinating reagents, or the conversion of the 4"-hydroxyl moiety into a leaving group, followed by treatment with a fluoride nucleophile, which leads to the products of the present invention or provide intermediates which are useful in their preparation.

Representative of the processes of the invention are reaction Schemes 1 and 2 presented below. In Scheme 1, erythromycin A, compound 7, is 2'-O-protected by treatment with an acid anhychide in a neutral inert solvent such as methylene or ethylene chloride to give compound 1. The O-protected product 1 is next treated with carbobenzoxy chloride to give the 4''-O-Cbz-protected compound 2. Treatment of compound 2 with an acid anhydride in an inert solvent such as methylene or ethylene chloride in the presence of a base or catalyst such as dimethylaminopyridine gives the 11-O-acetyl compound 3. Catalytic hydrogenation removes the Cbz-protecting group to give compound 4. Oxidation (for example, with N-chlorosuccinimide and dimethylsulfide) affords the 4''-keto compound 5. Catalytic hydrogenation affords the 4''-epi compound 6. Treatment of the 4''-epi compound with diethylaminosulfur trifluoride and dimethylaminopyridine in an inert solvent (for example, bis-2-methoxyethyl ether) affords the 3''-fluoro compound 7. Treatment of 7 with a protic solvent such as methanol leads to removal of the 2'-hydroxy protecting group to afford compound 8. Treatment of 8 with sodium alkoxide in alcohol affords the de-protected compound 9.

In Scheme 2, erythromycin A is reacted with ethylene carbonate and potassium carbonate to give the 11,12-O-cyclic carbonate 10. The 2'-hydroxy group is O-proteected with an acid anhydride in an inert solvent. The 4''-hydroxy group is oxidized (for example, with NCS and DMS) to give the 4''-keto compound 12. Catalytic hydrogenation (for example, with Raney nickel) gives the 4''-epi compound 13. Treatment of 13 with diethylaminosulfur trifluoride and dimethylaminopyridine gives either the enol ether 14, as the predominant product, if the reaction is run in methylene chloride or compound 16, as the predominant product, if the reaction is run in bis-2-methoxyethyl ether. Treatment of compounds 14 and 16 with methanol gives the desired de-protected compounds 15 and 17.

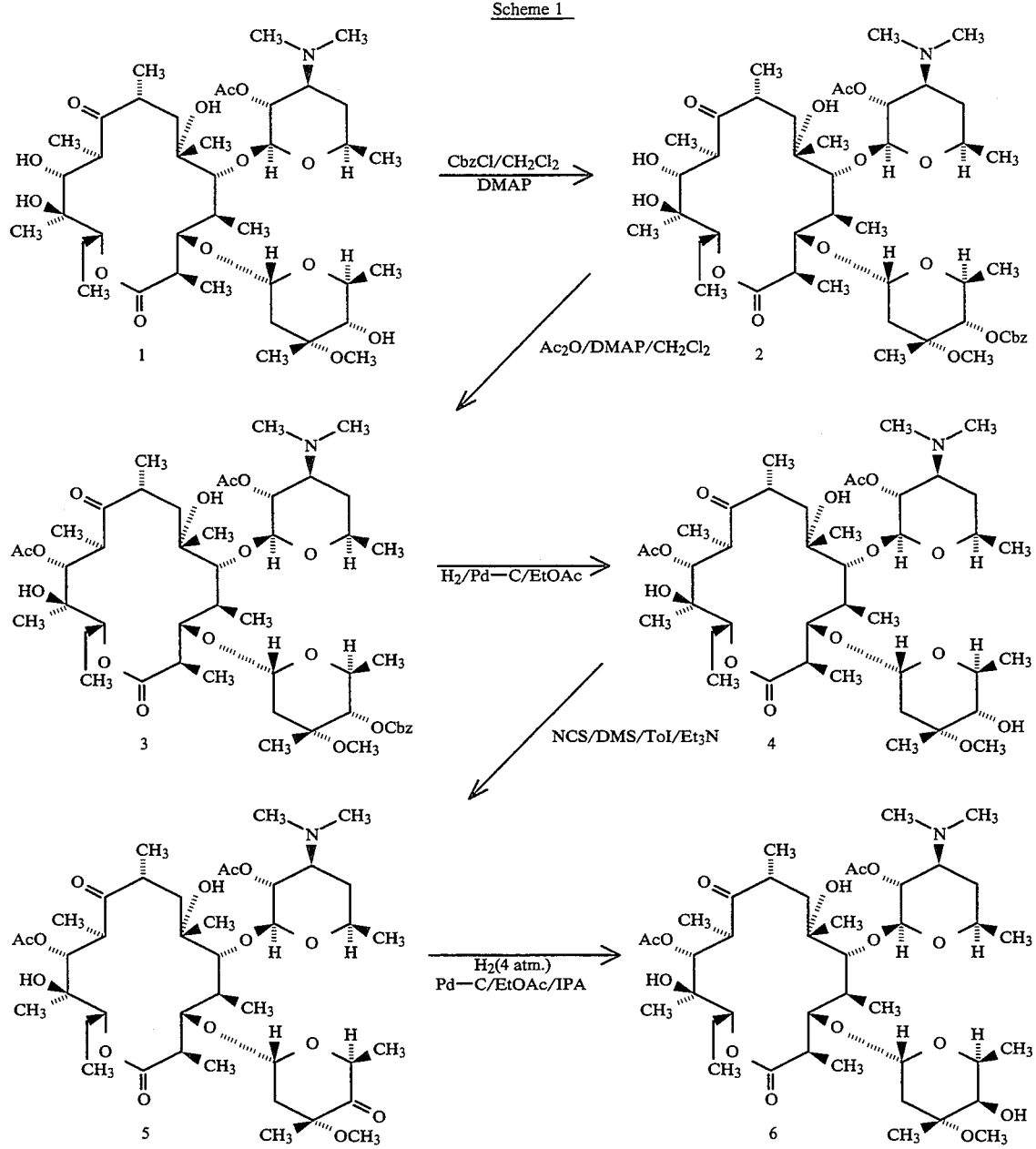

Scheme 1

-continued
Scheme 1
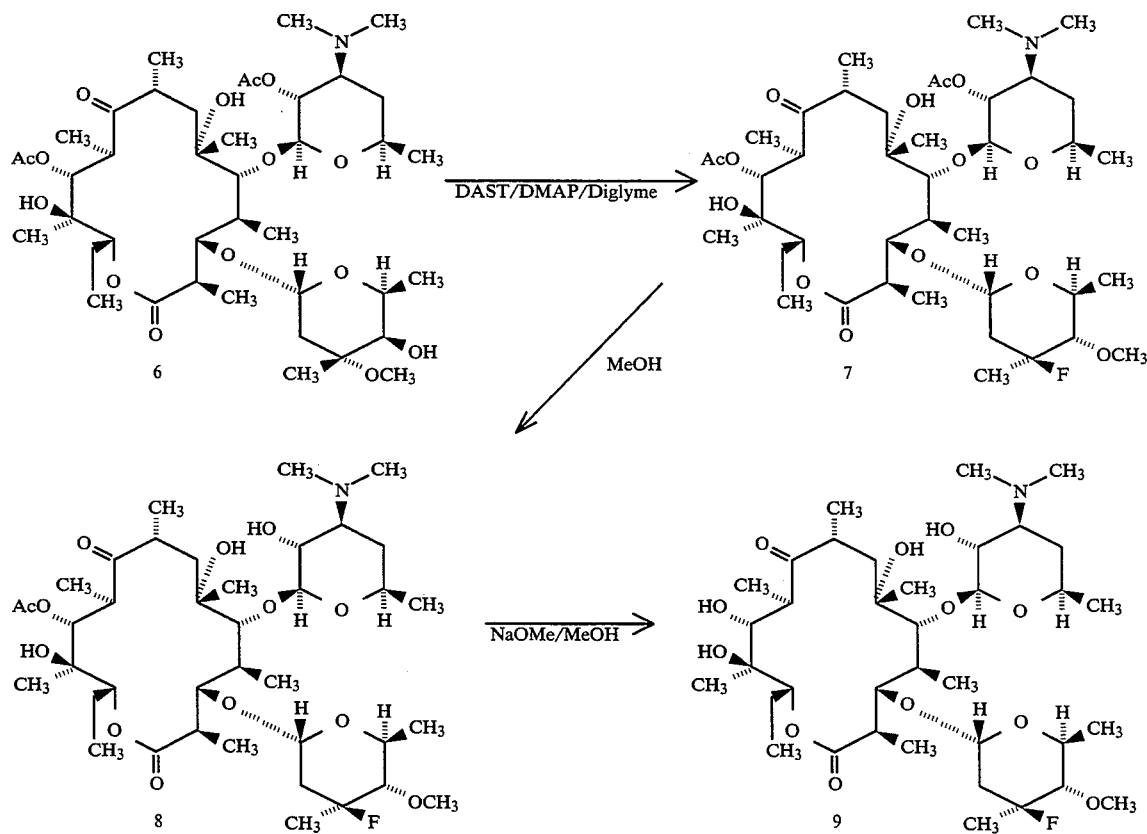
Scheme 2
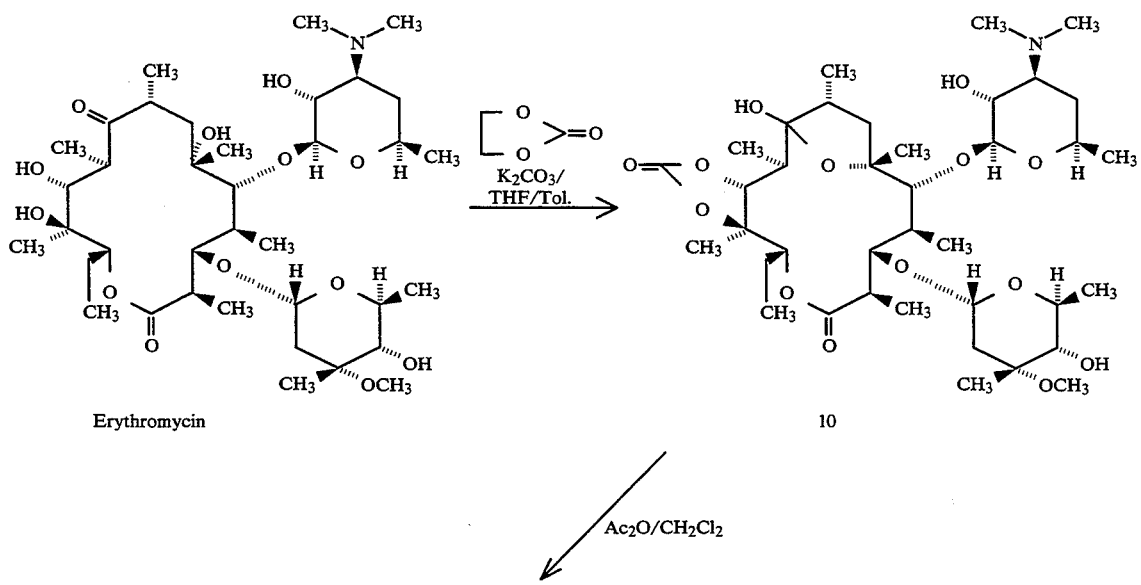

-continued
Scheme 2
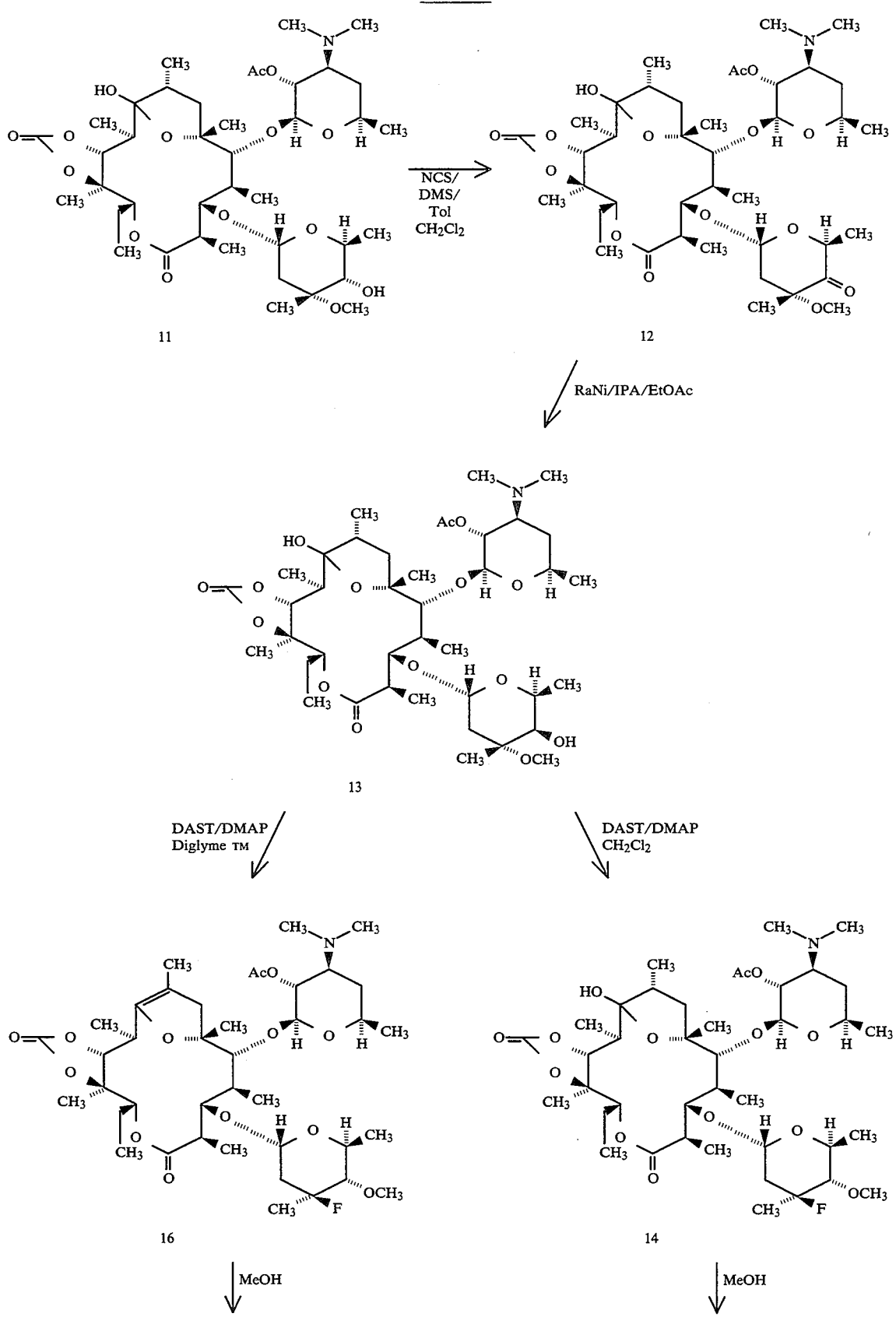

-continued
Scheme 2

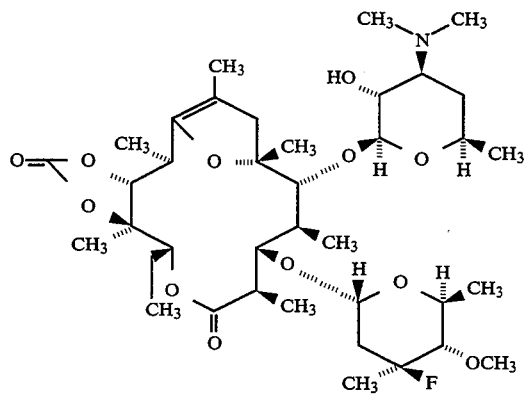

17

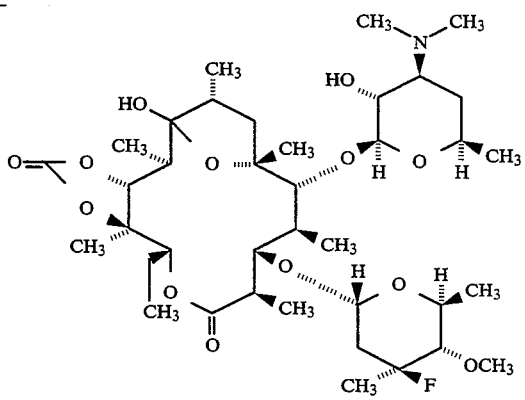

15

The above processes for preparing the compounds of the present invention will be better understood in connection with the following examples, which are intended as an illustration of and not a limitation upon the scope of the invention. In the Examples and elsewhere herein, the following abbreviations are used: Ac$_2$O for acetic anhydride, DAST for diethylaminosulfur trifluoride, DMAP for dimethylaminopyridine, DMS for dimethylsulfate, Et$_3$N for triethylamine, Et$_2$O for diethyl ether, EtOAc for ethyl acetate, NCS for N-chlorosuccinimide, and THF for tetrahydrofuran.

EXAMPLE 1

2'-O-Acetyl-erythromycin A

To erythromycin A (2.674 mmol) dissolved in 100 mL of CH$_2$Cl$_2$ at ambient temperature and then cooled to 0° C. was added 1.1 equivalents of Ac$_2$O (0.28 mL). The reaction mixture was allowed to warm to ambient temperature, stirred for 3 hours and extracted with CH$_2$Cl$_2$. The combined organic extracts were washed once with 8% sodium bicarbonate solution, tarice with water and once with brine, dried over Na$_2$SO$_4$ and concentrated in vacuo to afford the crude product as a white powder. Recrystallization from acetonitrile afforded the title compound.

EXAMPLE 2

2'-O-Acetyl-4"-O-benzyloxycarbonyl-erythromycin A

To the compound resulting from Example 1 (30 g, 38.7 mmol) and benzyloxychlorofonnate (17 mL) in CH$_2$Cl$_2$ (151 mL) was added dimethylaminopyridine (19 g). The solution was purged with nitrogen, cooled to −25° C. and stored overnight at that temperature. The reaction was quenched with phosphate buffer, diluted with CH$_2$Cl$_2$, washed with 5% sodium bicarbonate and brine, dried over Na$_2$SO$_4$ and concentrated in vacuo. Recrystallization from a minimum amount of CH$_3$CN afforded the title compound as a white crystalline solid.

EXAMPLE 3

2',11-Di-O-acetyl-4"-O-benzyloxycarbonylerythromycin A

To the compound resulting from Example 2 (15 g, 16.5 mmol) dissolved in CH$_2$Cl$_2$ (300 mL) was added DMAP (4.0 g) followed by Ac$_2$O (2.33 mL). The reaction mixture was stirred at ambient temperature for 2.5 hours and quenched with phosphate buffer, diluted with CH$_2$Cl$_2$, washed with 5% NaHCO$_3$, dried over Na$_2$SO$_4$ and concentrated in vacuo to give 16.6 g of the title compound.

EXAMPLE 4

2',11-Di-O-acetyl-erythromycin A

The compound resulting from Example 3 (10 g) was dissolved in EtOAc (250 mL) and treated with 1.0 g of 10% Pd/C under 4 atmospheres of H$_2$ at ambient temperature. Upon completion of the reaction, the catalyst was removed by filtration and the ffitrate concentrated in vacuo. The residue obtained was dissolved in CH$_2$Cl$_2$, washed with 5% NaHCO$_3$, dried over Na$_2$SO$_4$ and concentrated in vacuo. The residue was dissolved in CH$_2$Cl$_2$ and filtered through a micropore fdtration apparatus and concentrated to afford the title compound as a white amorphous solid (7.3 g).

EXAMPLE 5

2',11-Di-O-acetyl-4"-deoxy-4"-oxoerythromycin A

Dimethylsulfide (2.2 mL, 4 equivalents) was added via syringe to a −10° C. (ice/acetone) solution of NCS (3.0 g, 3 equivalents) dissolved in 90 mL of anhydrous toluene. The reaction was stirred at −10° C. for 20 minutes and then treated with a solution of the compound resulting from Example 4 (6.0 g, 7.34 mmol) dissolved in 40 mL of anhydrous toluene and 10 mL of anhydrous CH$_2$Cl$_2$. and stirred at −10° C. for 45 minutes. The reaction was quenched by the addition of Et$_3$N (3.2 mL) and poured into brine/CH$_2$Cl$_2$. The organic phase was washed with 5% NaHCO$_3$ and brine, dried over Na$_2$SO$_4$ and concentrated in vacuo to give 5.0 g of crude compound. Purification of ~800 mg of crude material on a silica gel column eluting with CHCl$_3$/CH$_3$CN/NH$_3$ provided 490 mg of the title compound as a white amorphous solid. MS (DCI/NH$_3$) m/e 815 (M+H)$^+$.

EXAMPLE 6

2',11-Di-O-acetyl-4"-epierythromycin A

The compound resulting from Example 5 (490 mg) was dissolved in EtOAc (75 mL) and isopropanol (75 mL) and treated with 1.0 g of 10% Pd/C under 4 atmospheres of H$_2$ for 18 hours. The catalyst was removed by filtration through a micropore filter and the filtrate concentrated in vacuo to give ~400 mg of the title compound. MS (DCI/NH$_3$) m/e 817 (M+H)$^+$.

EXAMPLE 7

(3″S)-2′,11-Di-O-acetyl-3″-desmthoxy-3″-fluoro-4″-O-methylerythromycin A

The compound resulting from Example 6 (400 mg, 0.489 mmol) was dissolved in bis-2-methoxyethyl ether (3 mL) and treated with DMAP (145 mg) and the system was flushed with $N_2$ and cooled to $-10°$ C. DAST (160 mL) was added and the solution was stirred at $-10°$ C. for 30 minutes and then diluted with toluene, washed with 5% $NaHCO_3$ and phosphate buffer, dried over $Na_2SO_4$ and concentrated in vacuo, followed by treatment with $CH_3OH$ and toluene to remove the bis-2-methoxyethyl ether, to afford ~250 mg of crude compound, which was purified by silica gel chromatography to give 20 mg of the title compound. MS ($DCI/NH_3$) m/e 819 $(M+H)^+$.

EXAMPLE 8

(3″S)-11-O-Acetyl-3″-desmethoxy-3″-fluoro-4″-O-methylerythromycin A

The compound resulting from Example 7 (70 mg) was stirred in $CH_3OH$ (1 mL) overnight at ambient temperature and concentrated in vacuo to afford the title compound. MS ($DCI/NH_3$) m/e 777 $(M+H)^+$.

EXAMPLE 9

(3″s)—3″-Desmethoxy-3″-fluoro-4″-O-methylerythromycin A

The compound resulting from Example 8 (17 mg) was dissolved in absolute $CH_3OH$ (1.5 mL), cooled in an ice bath and treated with 4 mL of NaOMe solution, prepared by dissolving 200 mg of Na metal in 3.8 mL of anhydrous $CH_3OH$, and stirred at ambient temperature overnight. An additional aliquot (2 mL) of NaOMe was added and stirring was continued for an additional hour. The reaction was quenched by the addition of $CH_2Cl_2$ and 5% $NaHCO_3$. The organic phase was washed with additional $NaHCO_3$ and the combined organic extracts were dried over $Na_2SO_4$ and concentrated in vacuo to afford ~13 mg of crude compound as an off-white amorphous solid which was purified by column chromatography on silica gel to give 1.4 mg of the title compound. MS ($DCI/NH_3$) m/e 735 $(M+H)^+$.

EXAMPLE 10

11-O,12-O-Carbonylerythromycin A

To Erythromycin A (40 g, 5.46 mmol) dissolved in THF (140 mL) and toluene (140 mL) was added ethylene carbonate (42.8 g, 8 equivalents) followed by crushed $K_2CO_3$ (24 g, 3.18 equivalents). The reaction mixture was heated to reflux and maintained at reflux for 5 hours. The reaction mixture was cooled to ambient temperature and quenched. Toluene was added and the solution was washed with phosphate buffer and 5% $NaHCO_3$, dried over $Na_2SO_4$ and concentrated in vacuo to give the crude title compound.

EXAMPLE 11

2′-O-Acetyl-11-O,12-O-carbonylerythromycin A

To the compound resulting from Example 10 (45 g, 59.3 mmol) dissolved in $CH_2Cl_2$ (300 mL) was added $K_2CO_3$ (21 g, 2.56 equivalents) followed by $Ac_2O$ (13.9 mL, 2.69 equivalents). The reaction mixture was stirred at ambient temperature for 3 hours and then worked up. The excess $Ac_2O$ was removed under reduced pressure and the residue obtained was dissolved in $CH_2Cl_2$ and 5% $NaHCO_3$. The organic phase was washed with brine, dried over $Na_2SO_4$ and concentrated in vacuo to afford the crude compound as a yellow oil. Purification by column chromatography on silica gel followed by recrystallization from a minimum amount of EtOAc afforded 8.82 g of the title compound as a white crystalline solid.

EXAMPLE 12

2′-O-Acetyl-11-O,12-O-carbonyl-4″-deoxy-4″-oxo-erythromycin A

A solution of N-chlorosuccinimide (1.5 g) was dissolved in 45 mL of toluene, flushed with $N_2$, cooled to $-10°$ C. and treated with 1.1 mL of dimethylsulfide. After stirring at $-10°$ C. for 20 minutes, a solution of the compound resulting from Example 11 (3.00 g) dissolved in 5 mL of $CH_2Cl_2$ was added. After 45 minutes at $-10°$ C., the reaction was quenched by the addition of $Et_3N$. The solution was diluted with toluene, washed with 5% $NaHCO_3$, dried over $Na_2SO_4$ and concentrated in vacuo. The residue obtained was recrystallized from a minimum amount of $Et_2O$ to give 2.1 g of the title compound as a white crystalline solid.

EXAMPLE 13

2′-O-Acetyl-11-O,12-0-carbonyl-4″-epierythromycin A

The compound resulting from Example 12 (1.94 g) was dissolved in 100 mL of isopropanol and 100 mL of EtOAc, treated with 3.9 g Raney nickel and placed under 4 atmospheres of $H_2$ at ambient temperature. Upon completion of the reaction, the catalyst was removed by filtration and the filtrate concentrated in vacuo. The residue was dissolved in $CH_2Cl_2$ and washed with 5% $NaHCO_3$, dried over $Na_2SO_4$ and concentrated in vacuo to afford 1.70 g of the title compound.

EXAMPLE 14

(3″S)-2′-O-Acetyl-11-O,12-O-carbonyl-3″-fluoro-3″-desmethoxy-4″-O-methylerythromycin A The compound resulting from Example 13 (100 mg, 0.125 mmol) was dissolved in $CH_2Cl_2$ (1.0 mL) and treated with DMAP (50 mg). The reaction mixture was flushed with $N_2$, cooled to $-10°$ C., treated with DAST (0.05 mL, 3 equivalents) dropwise and stirred at $-10°$ C. for 1 hour. After an additional 90 minutes at 0° C., the solution was diluted with $CH_2Cl_2$ and washed with 5% $NaHCO_3$, phosphate buffer and 5% $NaHCO_3$, dried over $Na_2SO_4$ and concentrated in vacuo to give the title compound as an amorphous solid (102 mg) which was purified by column chromatography on silica gel. MS ($DCI/NH_3$) m/e 803 $(M+H)^+$.

EXAMPLE 15

(3″S)-11-O,12-O-Carbonyl-3″-fluoro-3″-desmethoxy-4″-O-methylerythromycin A

The compound resulting from Example 14 (19 mg) was dissolved in methanol (2 mL) and stirred at ambient temperature for 24 hours. The solvent was removed under reduced pressure to afford the title compound (15.4 mg). MS ($DCI/NH_3$) m/e 761 $(M+H)^+$.

EXAMPLE 16

(3″S)-2′-O-Acetyl-8,9-anhydro-11-O,12-O-carbonyl-3″-fluoro-3″-desmethoxy-4″-O-methylerythromycin A-6,9-hemiketal The compound resulting from Example 13 (320 mg) was dissolved in bis-2-methoxyethyl ether (3 mL) and treated with DMAP (145 mg, 3 equivalents). The reaction mixture was flushed with $N_2$, cooled to $-10°$ C., treated with DAST (0.158 mL, 3 equivalents) dropwise and stirred at $-10°$ C. for 1 hour. After an additional hour at 0° C., the solution was diluted with $CH_2Cl_2$, washed with 5% $NaHCO_3$, phosphate buffer and 5% $NaHCO_3$, dried over $Na_2SO_4$ and concentrated in vacuo to give a syrup. EtOAc (50 mL) was added and the mixture was washed 8 times with 30 mL portion of brine followed by washes with phosphate buffer and 5% $NaHCO_3$, dried, and concentrated in vacuo to afford the title compound as an amorphous solid (330 mg). MS (DCI/$NH_3$) m/e 785 $(M+H)^+$.

EXAMPLE 17

(3″S)-8,9-Anhydro-11-O,12-O-carbonyl-3″-fluoro-3″-desmethoxy-4″-O-methylerythromycin A-6,9-hemiketal The compound resulting from Example 16 was dissolved in methanol and stirred at ambient temperature overnight. The solvent was removed under reduced pressure to afford the title compound. MS (DCI/$NH_3$) m/e 743 $(M+H)^+$.

EXAMPLE 18

Physical Characterization

The compounds resulting from the above Examples were characterized using nuclear magnetic resonance spectroscopy. The NMR data obtained are shown in Tables 1–3, below.

TABLE 1

| | $^1$H NMR | | | | | | | |
|---|---|---|---|---|---|---|---|---|
| | $^1$H NMR (δ PPM) in $CDCl_3$ | | | | | | | |
| Ex. # | 6-Me | 10 | 11 | 12-Me | 2′ | 3′ | 4″ | OMe |
| 5 | 1.25 | 2.25 | 5.02 | 1.50 | 4.75 | 2.75 | 3.20 | 3.31 |
| 6 | 1.25 | 2.20 | 4.90 | 1.50 | 4.78 | 2.70 | 3.09 | 3.40 |
| 7 | 1.25 | 2.22 | 4.95 | 1.50 | 4.75 | 2.70 | 3.05 | 3.57 |
| 8 | 1.26 | 2.22 | 4.98 | 1.50 | 3.25 | 2.53 | 3.01 | 3.54 |
| 9 | 1.22 | 1.76 | 2.59 | 1.08 | 3.35 | 2.56 | 2.96 | 3.52 |
| 14 | 1.58 | 1.95 | 4.93 | 1.46 | 4.81 | 2.73 | 3.04 | 3.57 |
| 15 | 1.57 | 1.98 | 4.90 | 1.47 | 3.30 | 2.51 | 3.00 | 3.52 |
| 16 | 1.45 | 2.84 | 4.19 | 1.55 | 4.75 | 2.75 | 3.01 | 3.50 |
| 17 | 1.34 | 2.84 | 4.20 | 1.40 | 3.14 | 2.44 | 3.00 | 3.54 |

TABLE 2

| | $^{19}$F NMR |
|---|---|
| Ex. # | $^{19}$F NMR (δ PPM from $CFCl_3$) in $CDCl_3$ |
| 7 | 130.2 |
| 8 | 130.1 |
| 9 | 129.9 |
| 14 | 129.3 |
| 15 | 129.2 |
| 16 | 129.3 |
| 17 | 129.8 |

TABLE 3

| | $^{13}$C NMR | | | | | | |
|---|---|---|---|---|---|---|---|
| | $^{13}$C NMR (d PPM) in $CDCl_3$ | | | | | | |
| Ex. # | 1 | 4 | 9 | 3′ | 3′-NMe | 3″ | 4″ |
| 5 | 176.0 | 40.6 | 108.8 | 63.5 | 40.6 | 72.8 | 211.3 |
| 6 | 176.8 | 40.8 | 108.3 | 63.1 | 40.3 | 70.5 | 79.1 |
| 7 | 176.1 | 40.6 | 108.9 | 63.4 | 40.6 | 98.3 | 86.2 |
| 8 | 176.4 | 40.2 | 108.5 | 65.2 | 40.4 | 97.0 | 86.2 |
| 9 | 175.2 | 40.3 | 221.2 | 65.6 | 40.3 | 97.3 | 85.9 |
| 14 | 177.8 | 41.3 | 110.4 | 63.2 | 40.6 | 97.0 | 86.5 |
| 15 | 177.5 | 42.0 | 109.8 | 64.9 | 40.5 | 96.7 | 86.5 |
| 16 | 176.3 | 43.6 | 147.8 | 63.7 | 40.3 | 95.8 | 86.3 |
| 17 | 176.8 | 43.4 | 147.6 | 65.7 | 40.3 | 96.0 | 86.3 |

EXAMPLE 19

In Vitro Assay of Antibacterial Activity

Representative compounds of the present invention were assayed in vitro for antibacterial activity as follows: Twelve petri dishes containing successive aqueous dilutions of the test compound mixed with 10 mL of sterilized Brain Heart Infusion (BHI) agar (Difco 0418-01-5) were prepared. Each plate was inoculated with 1:100 (or 1:10 for slow-growing strains, such as Micrococcus and Streptococcus) dilutions of up to 32 different microorganisms, using a Steers replicator block. The inoculated plates were incubated 35°–37° C. for 20 to 24 hours. In addition, a control plate, using BHI agar containing no test compound, was prepared and incubated at the beginning and end of each test.

An additional plate containing a compound having known susceptibility patterns for the organisms being tested and belonging to the same antibiotic class as the test compound was also prepared and incubated as a further control, as well as to provide test-to-test comparability. Erythromycin A was used for this purpose.

After incubation, each disk was read. The minimum inhibitory concentration (MIC) was defined as the lowest concentration of drug yielding no growth, a slight haze, or sparsely isolated colonies on the inoculum spot as compared to the growth control. The results of this assay, shown below in Table 4, support the conclusion that the compounds of the invention are effective antibacterial agents.

TABLE 4

| | | | MIC μg/mL | | |
|---|---|---|---|---|---|
| ORGANISM | STRAIN | CONTROL | Example 9 | Example 15 | Example 17 |
| *Staphylococcus aureus* | ATCC 6538P | 0.2 | 1.56 | 0.39 | 1.56 |
| *Staphylococcus aureus* | A5177 | 1.56 | 12.5 | 6.2 | 12.5 |
| *Staphylococcus aureus* | A5278 | >100 | >100 | >100 | 25 |
| *Staphylococcus aureus* | CMX 642a | 0.2 | 1.56 | 0.39 | 1.56 |
| *Staphylococcus aureus* | NCTC 10649 | 0.2 | 1.56 | 0.39 | 1.56 |
| *Staphylococcus aureus* | CMX 553 | 0.2 | 1.56 | 0.39 | 1.56 |
| *Staphylococcus aureus* | 1775 Cipro R | >100 | >100 | >100 | 25 |
| *Staphylococcus epidermidis* | 3519 | 0.2 | 1.56 | 0.39 | 1.56 |
| *Enterococcus faecium* | ATCC 8043 | 0.1 | 0.39 | 0.05 | 0.39 |
| *Streptococcus bovis* | A5169 | 0.05 | 0.2 | 0.01 | 0.1 |
| *Streptococcus agalactiae* | 508 | 0.05 | 0.39 | 0.05 | 0.2 |

TABLE 4-continued

| ORGANISM | STRAIN | CONTROL | MIC μg/mL Example 9 | Example 15 | Example 17 |
|---|---|---|---|---|---|
| Streptococcus pyogenes | EES61 | 0.05 | 0.39 | 0.05 | 0.2 |
| Streptococcus pyogenes | 930 const | >100 | >100 | >100 | 12.5 |
| Streptococcus pyogenes | 2548 induc | 6.2 | 3.1 | 0.39 | 1.56 |
| Micrococcus luteus | ATCC 9341 | 0.05 | 0.2 | 0.01 | 0.1 |
| Micrococcus luteus | 4698 | 0.39 | 0.39 | 0.1 | 1.56 |
| Escherichia coli | Juhl | 50 | >100 | 100 | >100 |
| Escherichia coli | SS | 0.39 | 1.56 | 0.2 | 3.1 |
| Escherichia coli | DC-2 | 100 | >100 | 100 | >100 |
| Escherichia coli | H560 | 50 | >100 | 50 | >100 |
| Escherichia coli | KNK 437 | 50 | >100 | 100 | >100 |
| Enterobacter aerogenes | ATCC 13048 | 100 | >100 | >100 | >100 |
| Klebsiella pneumoniae | ATCC 8045 | 50 | >100 | 100 | >100 |
| Providencia stuartii | CMX 640 | >100 | >100 | >100 | >100 |
| Pseudomonas aeruginosa | BMH10 | 100 | >100 | >100 | >100 |
| Pseudomonas aeruginosa | A5007 | >100 | >100 | >100 | >100 |
| Pseudomonas aeruginosa | K799/WT | >100 | >100 | 100 | >100 |
| Pseudomonas aeruginosa | K799/61 | 3.1 | 50 | 3.1 | 50 |
| Pseudomonas cepacia | 2961 | >100 | >100 | 25 | >100 |
| Acinetobacter calcoaceticus | CMX 669 | 1.56 | >100 | 100 | 25 |
| Pseudomonas aeruginosa | 5263 | >100 | >100 | >100 | >100 |
| Pseudomonas aeruginosa | 2862 | >100 | >100 | >100 | >100 |
| Candida albicans | CCH 442 | >100 | | | |
| Mycobacterium smegmatis | ATCC 114 | 12.5 | | | |
| Nocardia asteroides | ATCC 9970 | 0.2 | | | |

The present invention has been described in terms of specific embodiments set forth in detail. It should be understood, however, that these embodiments are presented by way of illustration only, and that the invention is not necessarily limited thereto. Modifications and variations within the spirit and scope of the claims that follow will be readily apparent from this disclosure, as those skilled in the art will appreciate.

What is claimed is:

1. A compound having the formula

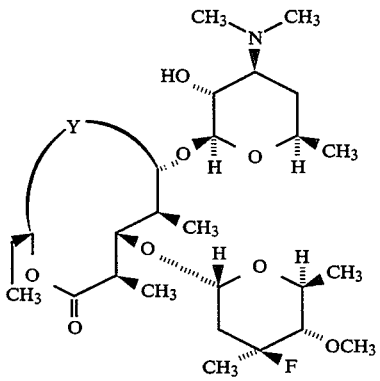

or a pharmaceutically acceptable salt thereof, wherein Y is selected from the group consisting of

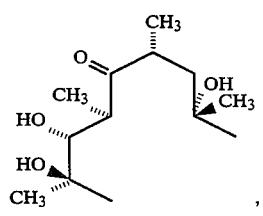

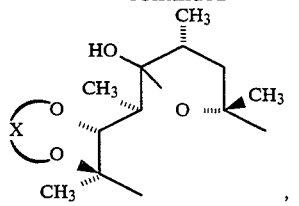

, and

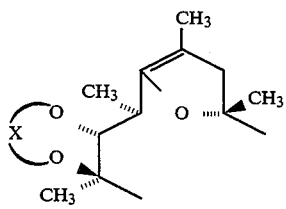

and X is selected from the group consisting of —C(O)—, —C(S)—, —CH₂—, —CH₂CH₂— and —C(CH₃)₂—.

2. A compound according to claim 1 wherein X is —C(O)—.

3. A compound selected from the group consisting of
(3"S)-3"-Desmethoxy-3"-fluoro-4"-O-methylerythromycin A;
(3"S)-11-O,12-O-Carbonyl-3"-fluoro-3"-desmethoxy-4"-O-methylerythromycin A;
(3"S)-8,9-Anhydro-11-O,12-O-carbonyl-3"-fluoro-3"-desmethoxy-4"-O-methylerythromycin A-6,9-hemiketal;
(3"S)-11-O,12-O-Thiocarbonyl-3"-fluoro-3"-desmethoxy-4"-O-methylerythromycin A;
(3"S)-8,9-Anhydro-11-O,12-O-thiocarbonyl-3"-fluoro-3"-desmethoxy-4"-O-methylerythromycin A-6,9-hemiketal;
(3"S)-11-O,12-O-Isopropylidene-3"-fluoro-3"-desmethoxy-4"-O-methylerythromycin A;
(3"S)-8,9-Anhydro-11-O,12-O-isopropylidene-3"-fluoro-3"-desmethoxy-4"-O-methylerythromycin A-6,9-hemiketal;
(3"S)-11-O,12-O-Ethylene-3"-fluoro-3"-desmethoxy-4"-O-methylerythromycin A;

(3″S)-8,9-Anhydro-11-O,12-O-ethylene-3″-fluoro-3″-desmethoxy-4″-O-methylerythromycin A-6,9-hemiketal;

(3″S)-11-O,12-O-Methylene-3″-fluoro-3″-desmethoxy-4″-O-methylerythromycin A; and (3″S)-8,9-Anhydro-11-O,12-O-methylene-3″-fluoro-3″-desmethoxy-4″-O-methylerythromycin A-6,9-hemiketal.

4. A compound according to claim 3 selected from the group consisting of (3″S)-3″-Desmethoxy-3″-fluoro-4″-O-methylerythromycin A;

(3″S)-11-O,12-O-carbonyl-3″-fluoro-3″-desmethoxy-4″-O-methylerythromycin A; and (3″S)-8,9-Anhydro-11-O,12-O-carbonyl-3″-fluoro-3″-desmethoxy-4″-O-methylerythromycin A-6,9-hemiketal.

5. A pharmaceutical composition useful for the treatment of bacterial infections, comprising a therapeutically effective amount of a compound according to claim 1 in combination with a pharmaceutically acceptable carrier.

6. A method for treating bacterial infections in a human or lower mammal, comprising administering to a patient in need of such treatment a therapeutically effective amount of a compound according to claim 1 for such time as is necessary to achieve a therapeutic effect.

* * * * *